US012534262B2

(12) United States Patent
Ippolito et al.

(10) Patent No.: US 12,534,262 B2
(45) Date of Patent: Jan. 27, 2026

(54) ORAL CARE SYSTEM

(71) Applicant: Sage Products, LLC, Cary, IL (US)

(72) Inventors: David Andrew Ippolito, Trout Valley, IL (US); Aaron M. Sunderlage, Palatine, IL (US); Nathan McHugh, Village of Lakewood, IL (US); Ron Klein, Crystal Lake, IL (US)

(73) Assignee: Sage Products, LLC, Cary, IL (US)

( * ) Notice: Subject to any disclaimer, the term of this patent is extended or adjusted under 35 U.S.C. 154(b) by 356 days.

(21) Appl. No.: 18/087,164

(22) Filed: Dec. 22, 2022

(65) Prior Publication Data

US 2023/0202702 A1 Jun. 29, 2023

Related U.S. Application Data

(60) Provisional application No. 63/293,460, filed on Dec. 23, 2021.

(51) Int. Cl.
*B65D 1/36* (2006.01)
*A61B 50/33* (2016.01)
*A61B 50/30* (2016.01)

(52) U.S. Cl.
CPC ................ *B65D 1/36* (2013.01); *A61B 50/33* (2016.02); *A61B 2050/3008* (2016.02)

(58) Field of Classification Search
CPC .... B65D 75/366; B65D 75/326; B65D 75/52; B65D 75/36; B65D 75/32; B65D 1/36; A61B 50/33; A61B 2050/3008
USPC ...................................... 206/581, 362.2, 561
See application file for complete search history.

(56) References Cited

U.S. PATENT DOCUMENTS

| | | | |
|---|---|---|---|
| 670,023 | A | 3/1901 | Jump |
| 884,256 | A | 4/1908 | Addie |
| 1,254,714 | A | 1/1918 | Mccombs |
| 1,283,403 | A | 10/1918 | Eustis |
| 1,705,050 | A | 3/1929 | Taylor |
| 1,723,944 | A | 8/1929 | Marsh |
| 1,770,478 | A | 7/1930 | Burnett |
| 2,084,540 | A | 6/1937 | Smith |

(Continued)

FOREIGN PATENT DOCUMENTS

| | | | |
|---|---|---|---|
| CA | D189737 | A | 12/2022 |
| DE | 29618648.9 | U1 | 12/1996 |

(Continued)

OTHER PUBLICATIONS

U.S. Appl. No. 29/683,163, filed Mar. 11, 2019.

(Continued)

*Primary Examiner* — Steven A. Reynolds
(74) *Attorney, Agent, or Firm* — FOLEY & LARDNER LLP

(57) ABSTRACT

An oral care tray that includes a top surface, a first compartment having a first bottom surface spaced from the top surface at a first vertical distance, and a second compartment having a second bottom surface spaced from the top surface at a second vertical distance. The oral care tray also includes a divider separating the first compartment and the second compartment thereby forming a first sidewall in the first compartment and a second sidewall in the second compartment, where the divider extends from the first bottom surface and the second bottom surface toward the top surface.

18 Claims, 12 Drawing Sheets

(56) References Cited

U.S. PATENT DOCUMENTS 2,161,854 A 6/1939 Copell
2,186,600 A 1/1940 Behrens
D143,320 S 12/1945 Horton
D145,045 S 6/1946 Plasket
D186,435 S 10/1959 Wilson
3,002,722 A 10/1961 Cote
3,220,543 A 11/1965 Mccord et al.
3,275,274 A 9/1966 Hutcheon
3,286,835 A 11/1966 Crane, Jr.
3,822,783 A 7/1974 Mortensen
3,840,932 A 10/1974 Balamuth et al.
3,927,762 A 12/1975 Zdarsky et al.
4,106,621 A * 8/1978 Sorenson ............. B65D 75/328 229/125.35
4,317,605 A 3/1982 Alissandratos
4,324,331 A 4/1982 Ignasiak
4,328,894 A 5/1982 Edell
4,570,652 A 2/1986 Chavez
D294,805 S 3/1988 Boyer
4,750,652 A 6/1988 Grant
4,854,760 A 8/1989 Unidec
4,880,111 A 11/1989 Bagwell et al.
4,915,219 A 4/1990 Ottimo
4,976,379 A 12/1990 Sloan
4,995,509 A 2/1991 Kornfeind
5,022,559 A 6/1991 Condon
5,095,924 A 3/1992 Stanfield
D332,401 S 1/1993 Araujo et al.
5,246,046 A 9/1993 Schramm
5,288,047 A 2/1994 Pan
5,379,895 A * 1/1995 Foslien .................. A61B 50/30 206/363
5,386,908 A 2/1995 Sinn
5,392,909 A 2/1995 Hackett
5,396,678 A 3/1995 Bredall et al.
5,445,631 A 8/1995 Uchida
D363,017 S 10/1995 Noble
D363,211 S 10/1995 Noble
D367,999 S 3/1996 Mccallum
5,495,876 A 3/1996 Schramm
D373,823 S 9/1996 Baldwin
5,765,254 A 6/1998 O'Halloran
5,816,408 A 10/1998 Indelicato
5,862,913 A 1/1999 Chou
RE36,131 E 3/1999 Schramm
5,908,057 A 6/1999 Schramm
5,950,648 A 9/1999 Skrocki et al.
6,059,106 A 5/2000 Baker et al.
6,082,999 A 7/2000 Tcherny et al.
D429,461 S 8/2000 Rowlay
6,108,849 A 8/2000 Weihrauch
6,131,737 A 10/2000 Marshall
6,213,777 B1 4/2001 Seitzinger
6,280,112 B1 8/2001 Vieu
6,283,311 B1 9/2001 Lee
6,311,837 B1 11/2001 Blaustein et al.
6,402,104 B1 6/2002 Smith
6,418,940 B1 7/2002 Tcherny et al.
6,543,100 B1 4/2003 Finley et al.
6,595,822 B1 7/2003 Thai
6,601,699 B1 8/2003 Naredo
6,638,131 B1 10/2003 Thai
6,702,113 B2 3/2004 Marino
6,857,928 B2 2/2005 Thai
6,889,829 B2 5/2005 Lev et al.
D508,200 S 8/2005 Cagle
6,945,397 B2 9/2005 Brattesani et al.
D510,822 S 10/2005 Spiers et al.
D512,908 S 12/2005 Proudfit
D513,382 S 1/2006 Proudfit
D520,356 S 5/2006 Kellar et al.
D523,610 S 6/2006 Kissell
7,124,894 B1 10/2006 Dobos
RE39,443 E 12/2006 Schramm
7,244,161 B2 7/2007 Thai
7,320,398 B2 1/2008 Bertl et al.
D571,207 S 6/2008 Rozanski
D571,208 S 6/2008 Rozanski
7,399,133 B1 7/2008 Eversole
7,524,230 B2 4/2009 Thai
D597,829 S 8/2009 Ma et al.
D614,489 S 4/2010 Doster
7,784,429 B2 8/2010 Chiodo
D630,528 S 1/2011 Dombrowski et al.
7,967,519 B2 6/2011 Gueret
RE42,610 E 8/2011 Schramm
8,091,702 B1 1/2012 Keip
D654,288 S 2/2012 Lecoutre
D654,724 S 2/2012 Lecoutre
D660,690 S 5/2012 Mixides
8,181,786 B1 5/2012 Alas
8,245,844 B2 8/2012 Sorrentino et al.
8,251,076 B2 8/2012 Souza
D666,903 S 9/2012 Mcintosh et al.
D681,444 S 5/2013 Oja et al.
8,506,192 B2 8/2013 Allbritton
D691,884 S 10/2013 Kwon
D698,639 S 2/2014 Fletcher et al.
8,734,420 B2 5/2014 Ariagno et al.
8,789,701 B2 * 7/2014 Hohlbein ........... B65D 75/5822 229/87.05
D715,641 S 10/2014 Spinos
D752,427 S 3/2016 Moskovich et al.
D767,393 S 9/2016 Giorgis
9,456,956 B1 10/2016 Webster et al.
D803,678 S 11/2017 Chen et al.
D803,679 S 11/2017 Chen et al.
9,833,605 B2 12/2017 Sanders et al.
D806,530 S 1/2018 Mack
D813,660 S 3/2018 Tyner
D816,478 S * 5/2018 Moskovich .................... D9/415
D826,706 S 8/2018 Moskovich et al.
10,058,649 B2 8/2018 Le Maner
D829,544 S 10/2018 Kocon et al.
10,327,539 B2 6/2019 Beck et al.
D853,226 S 7/2019 Geringer et al.
D853,831 S 7/2019 Geringer et al.
10,687,612 B2 6/2020 Beck et al.
D901,312 S 11/2020 Fowler et al.
D954,551 S 6/2022 Moak et al.
D988,868 S 6/2023 Fowler et al.
D995,288 S 8/2023 Okoroafor et al.
12,029,311 B2 7/2024 Blabas et al.
2001/0032796 A1 10/2001 Rubenstein
2001/0035413 A1 11/2001 Thai
2002/0121449 A1 9/2002 Bowie
2004/0129580 A1 7/2004 Cochran et al.
2004/0211683 A1 10/2004 Barham et al.
2004/0240928 A1 12/2004 Trocino
2005/0087464 A1 4/2005 Brattesani et al.
2005/0161454 A1 7/2005 Nehren et al.
2006/0021166 A1 2/2006 Hills
2006/0048791 A1 3/2006 Mehes et al.
2006/0131189 A1 6/2006 Lee et al.
2006/0208142 A1 9/2006 Adams
2006/0260635 A1 11/2006 Dabney
2006/0289030 A1 12/2006 Pho
2007/0220754 A1 9/2007 Barbaro et al.
2008/0209650 A1 9/2008 Brewer et al.
2009/0159487 A1 6/2009 Tacoma
2009/0197220 A1 8/2009 Cindrich
2011/0297574 A1 12/2011 Lecoutre
2012/0048760 A1 3/2012 Karey et al.
2012/0170967 A1 7/2012 Faison
2012/0241347 A1 9/2012 Bowers et al.
2013/0037441 A1 2/2013 Pacheco
2013/0140310 A1 6/2013 Lien et al.
2013/0230349 A1 9/2013 Dontfraid
2013/0340185 A1 12/2013 Patel et al.
2014/0008266 A1 * 1/2014 Lee ....................... B65D 75/54 206/581
2015/0014492 A1 1/2015 Sharpe et al.
2015/0282603 A1 10/2015 Jimenez et al.
2016/0039393 A1 2/2016 Zhuo

(56) References Cited

U.S. PATENT DOCUMENTS

| | | | |
|---|---|---|---|
| 2016/0198990 | A1 | 7/2016 | Betancur et al. |
| 2016/0206412 | A1 | 7/2016 | Bock |
| 2017/0095071 | A1 | 4/2017 | Osmond et al. |
| 2017/0311707 | A1 | 11/2017 | Beck et al. |
| 2018/0071506 | A1 | 3/2018 | Sanders et al. |
| 2018/0085515 | A1* | 3/2018 | Mide ..................... A61M 5/002 |
| 2018/0132605 | A1 | 5/2018 | Fowler et al. |
| 2018/0132989 | A1 | 5/2018 | Deane et al. |
| 2018/0161491 | A1 | 6/2018 | Sanders et al. |
| 2018/0161492 | A1 | 6/2018 | Sanders et al. |
| 2018/0168786 | A1 | 6/2018 | Meng et al. |
| 2018/0352948 | A1* | 12/2018 | Bryzek .............. B65D 77/0406 |
| 2019/0307237 | A1 | 10/2019 | Beck et al. |
| 2020/0305589 | A1 | 10/2020 | Beck et al. |
| 2020/0390230 | A1 | 12/2020 | Fowler et al. |
| 2020/0405046 | A1 | 12/2020 | Deane et al. |
| 2021/0059393 | A1 | 3/2021 | Yang et al. |
| 2022/0015526 | A1 | 1/2022 | Fowler et al. |
| 2022/0177211 | A1 | 6/2022 | Beck et al. |
| 2022/0225757 | A1 | 7/2022 | Fowler et al. |
| 2023/0092350 | A1 | 3/2023 | Fowler et al. |
| 2023/0240436 | A1 | 8/2023 | Gross et al. |
| 2023/0248183 | A1 | 8/2023 | Mclain |

FOREIGN PATENT DOCUMENTS

| | | | |
|---|---|---|---|
| EM | 006852877-0001 | | 9/2019 |
| EM | 006852877-0002 | | 9/2019 |
| EM | 006852877-0003 | | 9/2019 |
| FR | 2606615 | A | 5/1988 |
| GB | 9 006 852877-0001 | | 9/2019 |
| GB | 9 006 852877-0002 | | 9/2019 |
| GB | 9 006 852877-0003 | | 9/2019 |
| JP | 08-052210 | A | 2/1996 |
| JP | 3059317 | U | 7/1999 |
| JP | 2000-159266 | A | 6/2000 |
| JP | 2002-234553 | A | 8/2002 |
| JP | 2002-539039 | A | 11/2002 |
| JP | 2010-013186 | A | 1/2010 |
| JP | 1725082 | S | 9/2022 |
| KR | 10-2009-0133048 | A | 12/2009 |
| KR | 20090133048 | A | 12/2009 |
| KR | 1020100050871 | A | 5/2010 |
| KR | 20130094557 | A | 8/2013 |
| KR | 101645283 | B1 | 8/2016 |
| WO | WO-00/58164 | A1 | 10/2000 |
| WO | WO-2012/087317 | | 6/2012 |
| WO | WO-2013/090659 | | 6/2013 |
| WO | WO-2016/059035 | | 4/2016 |
| WO | WO-2018/090050 | | 5/2018 |
| WO | WO-2020/118235 | | 6/2020 |
| WO | WO-2022/001607 | | 1/2022 |
| WO | WO-2022/016075 | A1 | 1/2022 |

OTHER PUBLICATIONS

International Search Report and Written Opinion for International Application No. PCT/US2019/065042, mailed Apr. 7, 2020, 11 pages.

International Search Report and Written Opinion for International Application No. PCT/US2021/042012, mailed Oct. 28, 2021, 17 pages.

International Search Report and Written Opinion for International Application No. PCT/US2021/061716, mailed Mar. 7, 2022, 16 pages.

Invitation to Pay Additional Fees for International Application No. PCT/US2019/065042, mailed Feb. 10, 2020, 2 pages.

PCT Collaborative Search and Examination Pilot, Peer ISA China National Intellectual Property, International Search Report and Written Opinion for International Application No. PCT/US2019/065042, completed Feb. 28, 2020, 13 pages.

PCT Collaborative Search and Examination Pilot, Peer ISA European Patent Office, International Search Report and Written Opinion for International Application No. PCT/US2019/065042, completed Feb. 18, 2020, 10 pages.

PCT Collaborative Search and Examination Pilot, Peer ISA Japan Patent Office, International Search Report and Written Opinion for International Application No. PCT/US2019/065042, completed Mar. 4, 2020, 9 pages.

PCT Collaborative Search and Examination Pilot, Peer ISA Korean Intellectual Property Office, International Search Report and Written Opinion for International Application No. PCT/US2019/065042, completed Mar. 6, 2020, 16 pages.

Pharmacy Counter Space Cardboard Display Box For Medicine Drugs. [online] Published on Sep. 22, 2018. Retrieved Jan. 3, 2020 from URL: http://www.cardboardpalletdisplay.com/sale-6122822-pharmacy-counter-space-cardboard-display-box-for-medicine-drugs.html.

Sage Self Oral Care Toothbrush. [online] Published on Nov. 30, 2019. Retrieved Jan. 3, 2020 from URL: https://www.stryker.com/us/en/sage/products/sage-self-oral-care.html.

Translation of KR 10-2009-0133048 A; provided by International Searching Authority for International Search Report and Written Opinion of International Application No. PCT/US2019/065042, mailed Apr. 7, 2020, 4 pages.

Sage Self Oral Care, posted date not available [retrieved Aug. 28, 2023]. Retrieved from internet, https:/Avww.stryker.com/us/en/sage/products/sage-self-oral-care.html (Year: 2023) 12 pages.

Suction Toothbrush Kit Sage, posted date not available [retrieved Aug. 28, 2023]. Retrieved from internet, https://mms.mckesson.com/product/1177792/Sage-Products-6301 (Year: 2023) 3 pages.

* cited by examiner

ORAL CARE SYSTEM

CROSS-REFERENCE TO RELATED APPLICATIONS

This application claims the benefit of and priority to U.S. Provisional Patent Application 63/293,460, filed Dec. 23, 2021, which is hereby incorporated by reference in its entirety.

BACKGROUND

The present disclosure relates generally to oral care systems. More specifically, the present disclosure relates to apparatuses, systems, and kits associated with an oral care tray.

Standard oral care device trays, containers and packaging are not ideally suited for use in hospitals and other medical treatment facilities where patients have compromised immune systems. For example, after use of a standard oral care device (e.g., a standard toothbrush), patients often place the oral care device back into a wrapper or kit with which the oral care device was provided. Placing oral care devices back into wrappers or kits after use has been shown to retain moisture and promote microbial growth. Further, in some instances patients place the oral care device on a nearby surface after use. Placing oral care devices directly on potentially contaminated surfaces can lead to cross-contamination and bacterial spreading. Further, repeated use of the standard oral care device increases the risk of bacterial infection and/or the spread of other illness and/or infection.

The present disclosure seeks to overcome certain of these limitations and other drawbacks of existing oral care systems used in hospital and/or other medical treatment facilities, and provide new features that are not heretofore available.

SUMMARY

At least one embodiment relates to an oral care tray. The oral care tray includes a top surface, a first compartment having a first bottom surface spaced from the top surface at a first vertical distance, and a second compartment having a second bottom surface spaced from the top surface at a second vertical distance. The oral care tray also includes a divider separating the first compartment and the second compartment thereby forming a first sidewall in the first compartment and a second sidewall in the second compartment, where the divider extends from the first bottom surface and the second bottom surface toward the top surface.

Another embodiment relates to an oral care system. The oral care system includes an oral care device, and an oral care tray configured to house the oral care device. The oral care tray includes a top surface, a first compartment having a first bottom surface spaced from the top surface at a first vertical distance, and a second compartment having a second bottom surface spaced from the top surface at a second vertical distance. The oral care tray also includes a divider separating the first compartment and the second compartment thereby forming a first sidewall in the first compartment and a second sidewall in the second compartment, where the divider extends from the first bottom surface and the second bottom surface toward the top surface.

Another embodiment relates to an oral care kit. The oral care kit includes an oral care device, a first container configured to house an oral care solution, and an oral care tray configured to house the oral care device. The oral care tray includes a top surface, a first compartment having a first bottom surface spaced from the top surface at a first vertical distance, and a second compartment having a second bottom surface spaced from the top surface at a second vertical distance. The oral care tray also includes a divider separating the first compartment and the second compartment thereby forming a first sidewall in the first compartment and a second sidewall in the second compartment, where the divider extends from the first bottom surface and the second bottom surface toward the top surface.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the Figures, systems, apparatuses, kits, and methods associated with an oral care tray are shown, according to various embodiments. The oral care tray may include a top surface, a first compartment having a first bottom surface spaced from the top surface at a first vertical distance, and a second compartment having a second bottom surface spaced from the top surface at a second vertical distance. The oral care tray also includes a divider separating the first compartment and the second compartment thereby forming a first sidewall in the first compartment and a second sidewall in the second compartment, where the divider extends from the first bottom surface and the second bottom surface toward the top surface. After use of an oral care device, the oral care tray may be configured to house the oral care device, such that a first portion of a base of the oral care device is housed in the first compartment, and a second portion of the base engages the divider. Advantageously, the oral care device is positioned such that a head of the oral care device is elevated and/or positioned away from the oral care tray, such that the head may adequately dry and/or avoid contact with potentially contaminated surfaces.

Figure 1:
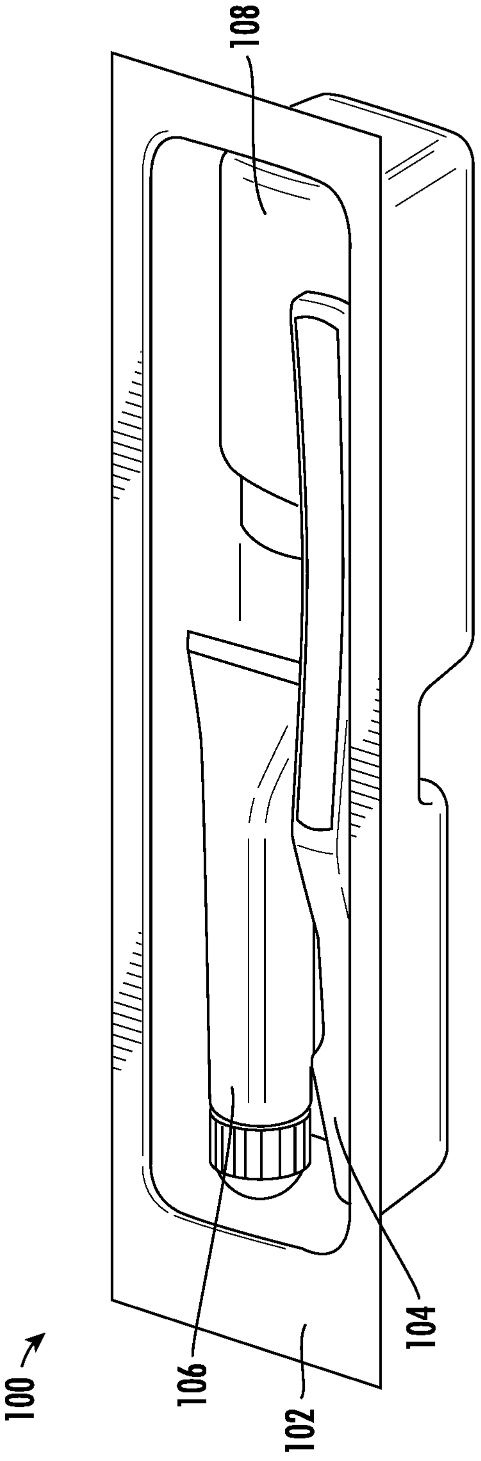
FIG. 1 is a top perspective view of an oral care system, according to an exemplary embodiment.
Figure 2:
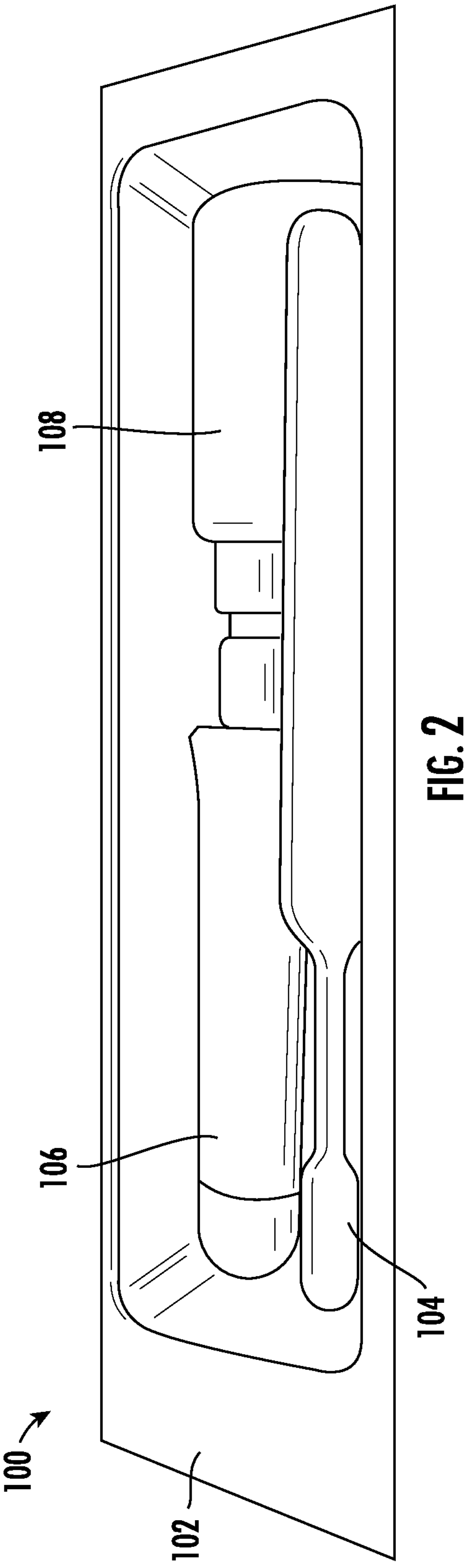
FIG. 2 is an alternative top perspective view of the oral care system of FIG. 1, according to an exemplary embodiment.

Referring now to FIGS. 1-2, top views of an oral care system are shown, according to an exemplary embodiment. The elements of the oral care system 100 may be configured for cleaning and/or care within an oral cavity, and for storing the elements of the oral care system 100 before and/or between uses. The oral care system 100 is shown to include an oral care tray 102, an oral care device 104, a first container 106, and a second container 108. In some embodiments, the oral care system 100 may include only the oral care tray 102, the oral care device 104, the first container 106, or the second container 108, or any combination thereof. In an exemplary embodiment, the oral care tray 102 is configured to house the oral care device 104, the first container 106, and/or the second container 108, for example during transportation, storage, and/or prior to use of the oral care device 104. The first container 106 and/or the second container 108 may be configured to house an oral care product (e.g., hydrogen peroxide solution, antiseptic oral rinse, oral moisturizer spray, mouth moisturizer, mouth paste, etc.), and selectively release the oral care product in response to manipulation. The oral care device 104 may receive an oral care product (e.g., from the first container 106, the second container 108, etc.), and/or the oral care product may be provided into an oral cavity. According to an exemplary embodiment, the oral care tray 102 is also configured to house the oral care device 104 (or a portion thereof), the first container 106, and/or the second container 108 between and/or after use of the oral care device 104. As will be discussed in greater detail below, in this regard the oral care system 100 may be configured to house (e.g., store) oral care devices and products between use, so as to reduce the risk of bacterial infection and/or the spread of other illnesses and/or infection.

Referring now to FIGS. 3-9, various views of the oral care tray 102 are shown, according to an exemplary embodiment. The oral care tray 102 may be configured to house the oral care device 104, the first container 106, the second container 108, and/or any other suitable oral care device and/or solution. The oral care tray 102 is shown to be generally rectangular, and may be formed of plastic material (e.g., high-density polyethylene, linear low-density polyethylene, low density polyethylene, ethylene vinyl alcohol, polylactic acid, thermoplastic elastomer, etc.). In other embodiments, the oral care tray 102 is another suitable shape, and/or formed of another suitable material.

According to an exemplary embodiment, the oral care tray 102 includes a top surface 120 positioned along a first plane, a first compartment 122 formed by a recessed portion of the tray or first recess, a second compartment 124 formed by a second recessed portion of the tray or second recess, and a divider 126. The top surface 120 may include an interface, which may be configured to engage a seal (e.g., a plastic, foil, etc. seal) so as to selectively seal the oral care tray 102 and/or oral care devices or solutions housed therein. The first compartment 122 and the second compartment 124 may be configured to house the oral care device 104, the first container 106, and/or the second container 108, and may be separated by the divider 126.

Figure 3:
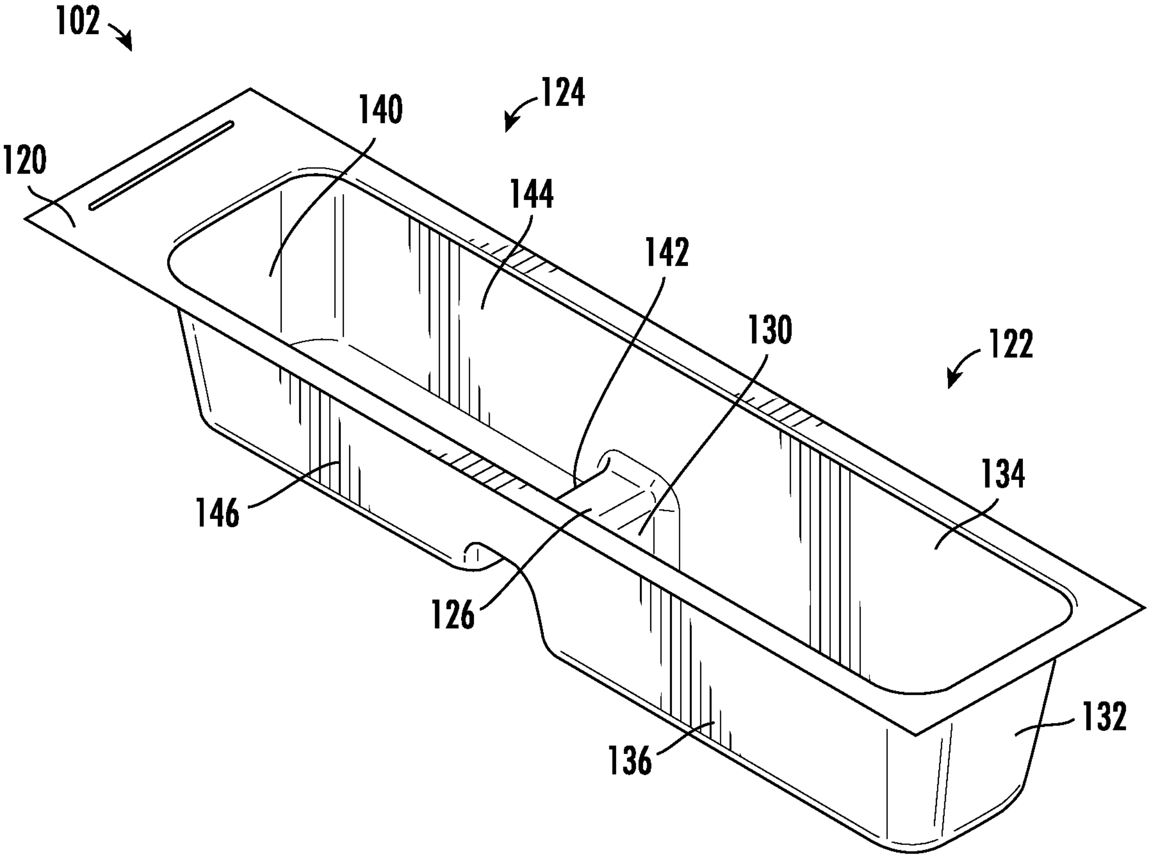
FIG. 3 is a perspective view of an oral care tray of the oral care system of FIG. 1, according to an exemplary embodiment.
Figure 4:
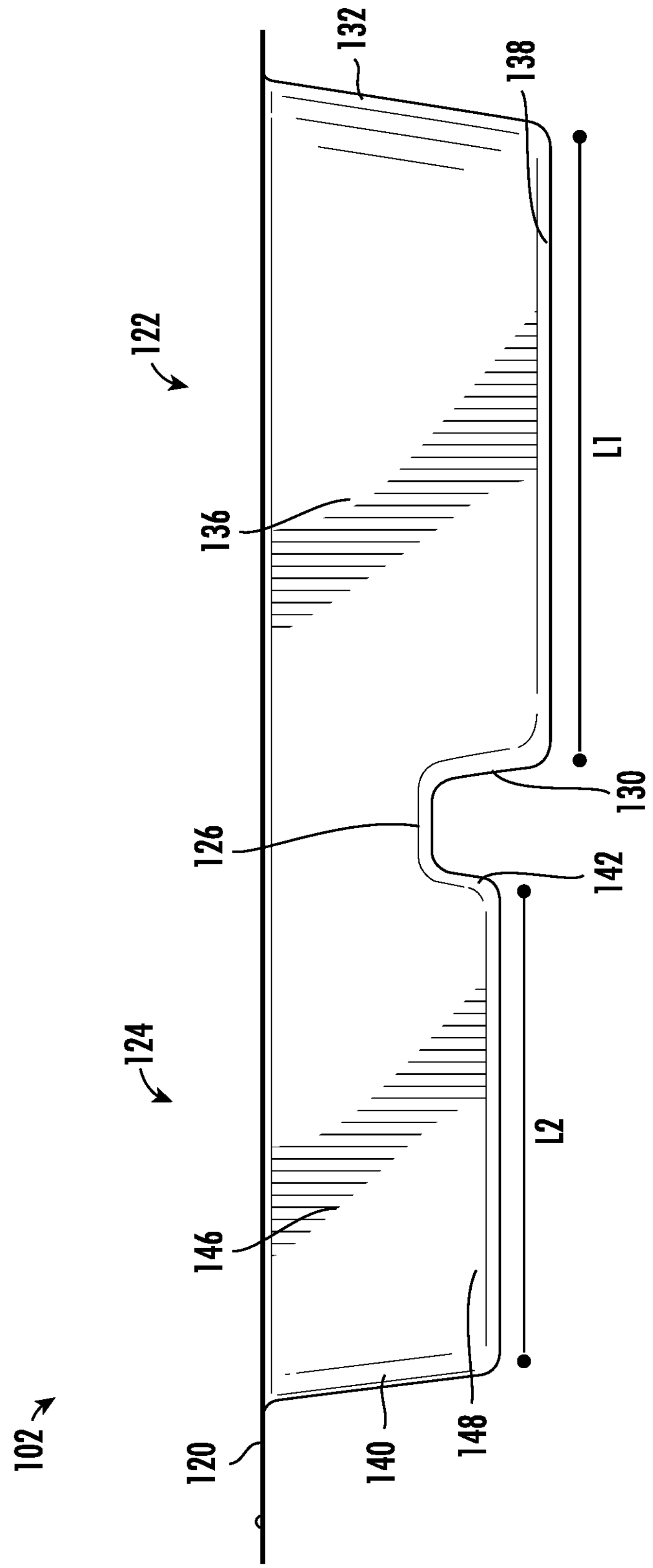
FIG. 4 is a left side view of the oral care tray of FIG. 3, according to an exemplary embodiment.
Figure 5:
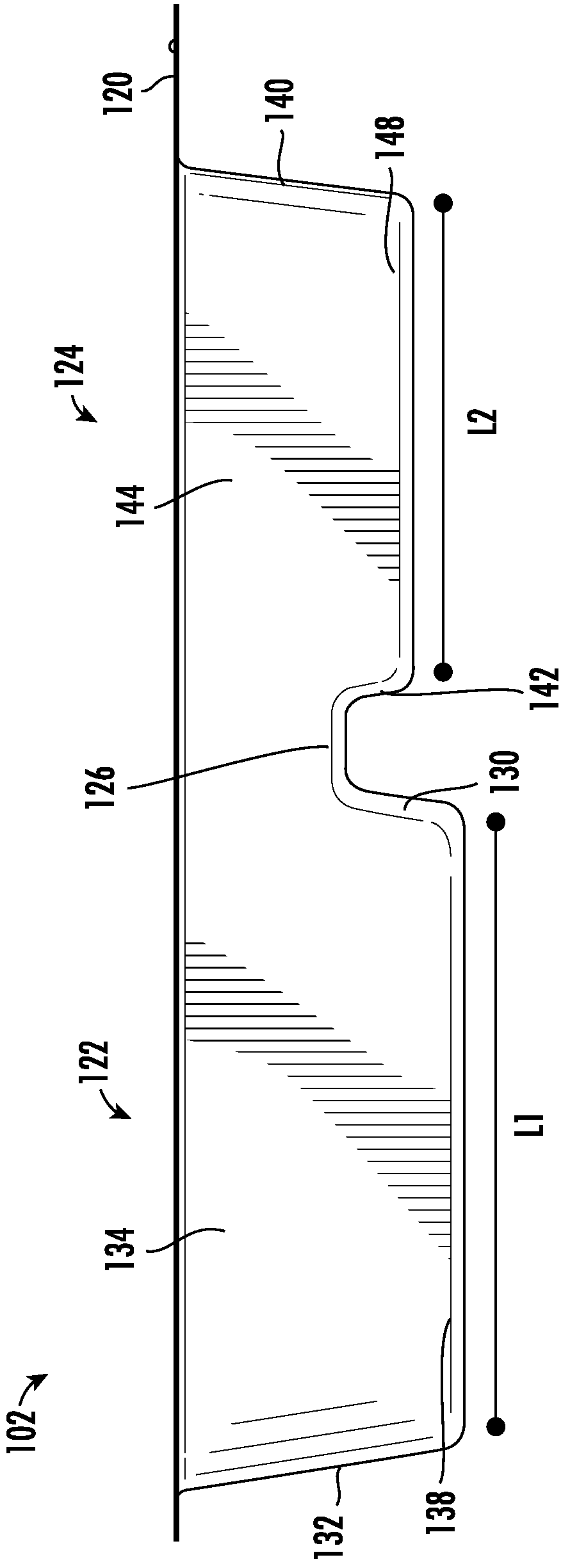
FIG. 5 is a right side view of the oral care tray of FIG. 3, according to an exemplary embodiment.
Figure 6:
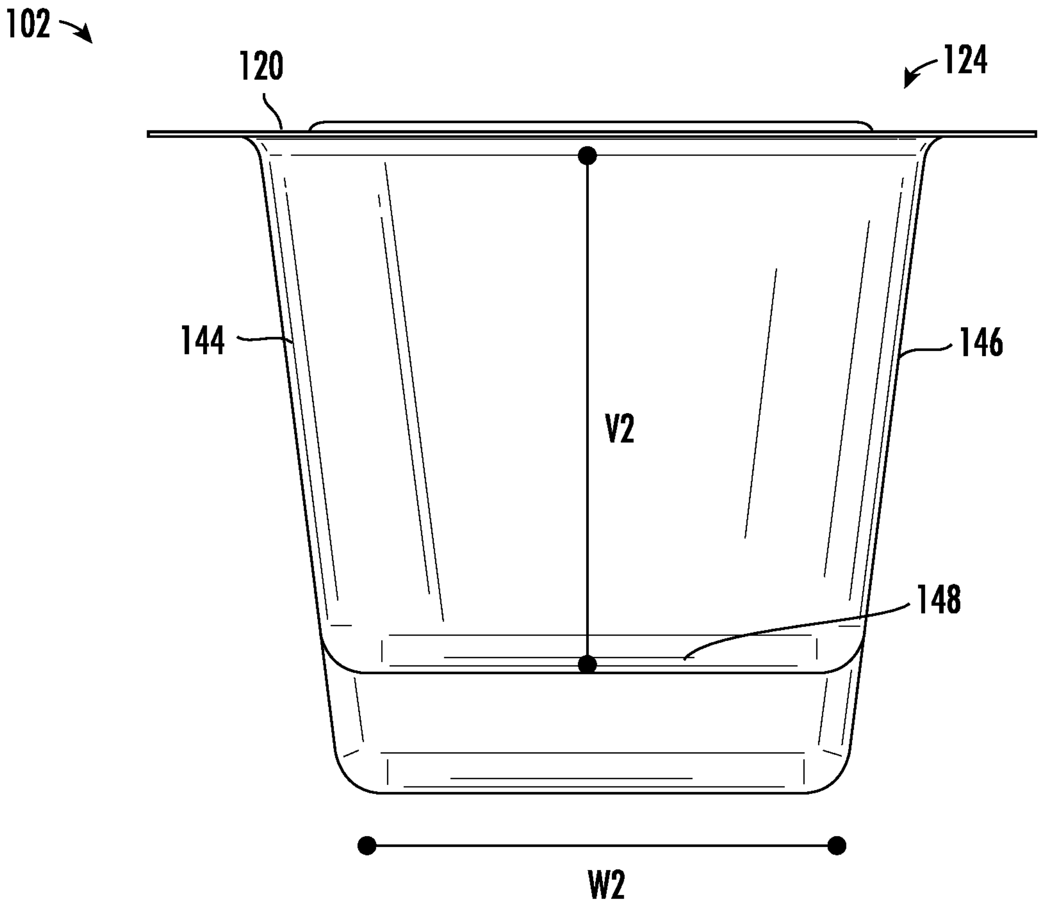
FIG. 6 is a front view of the oral care tray of FIG. 3, according to an exemplary embodiment.
Figure 7:
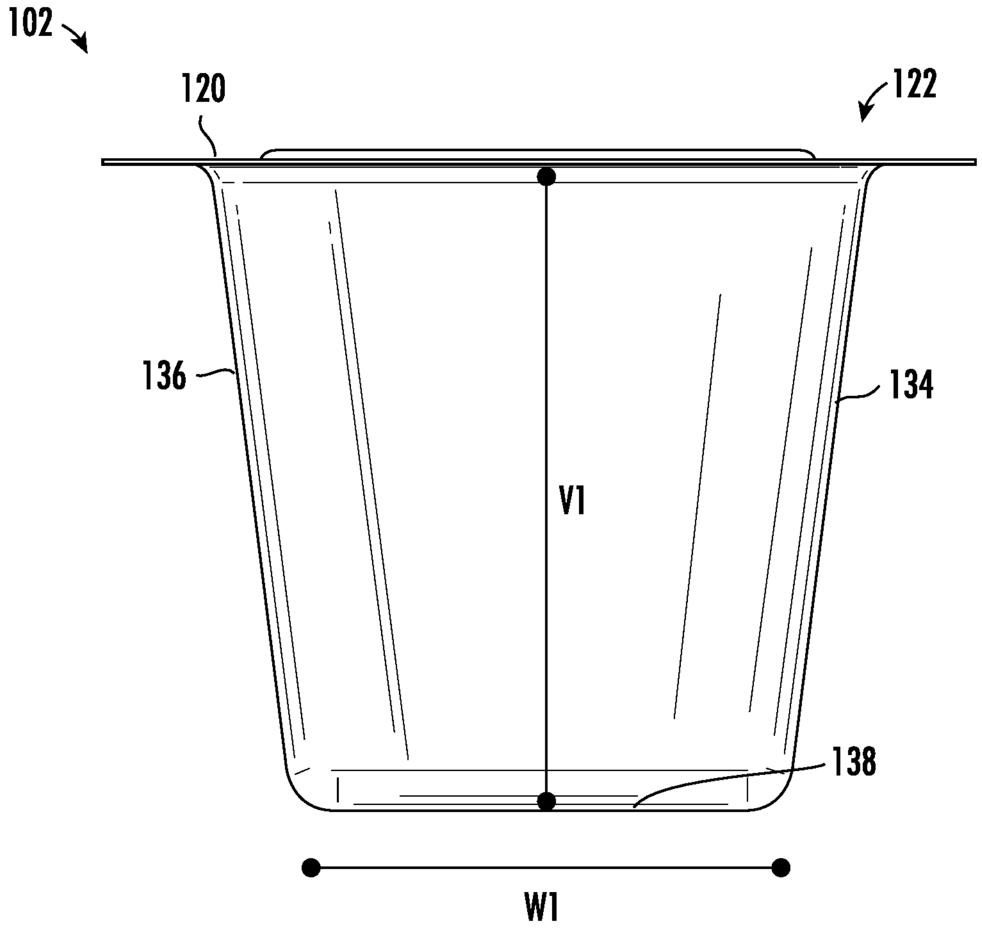
FIG. 7 is a rear view of the oral care tray of FIG. 3, according to an exemplary embodiment.
Figure 8:
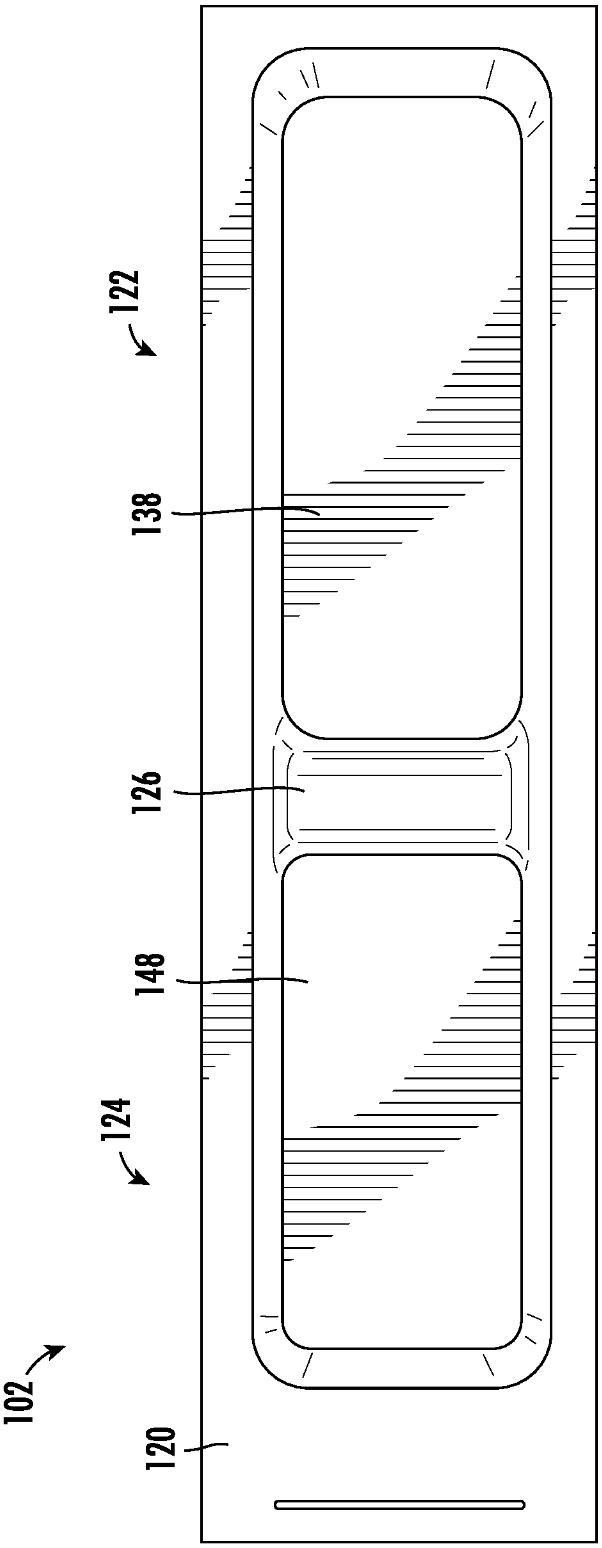
FIG. 8 is a top view of the oral care tray of FIG. 3, according to an exemplary embodiment.
Figure 9:
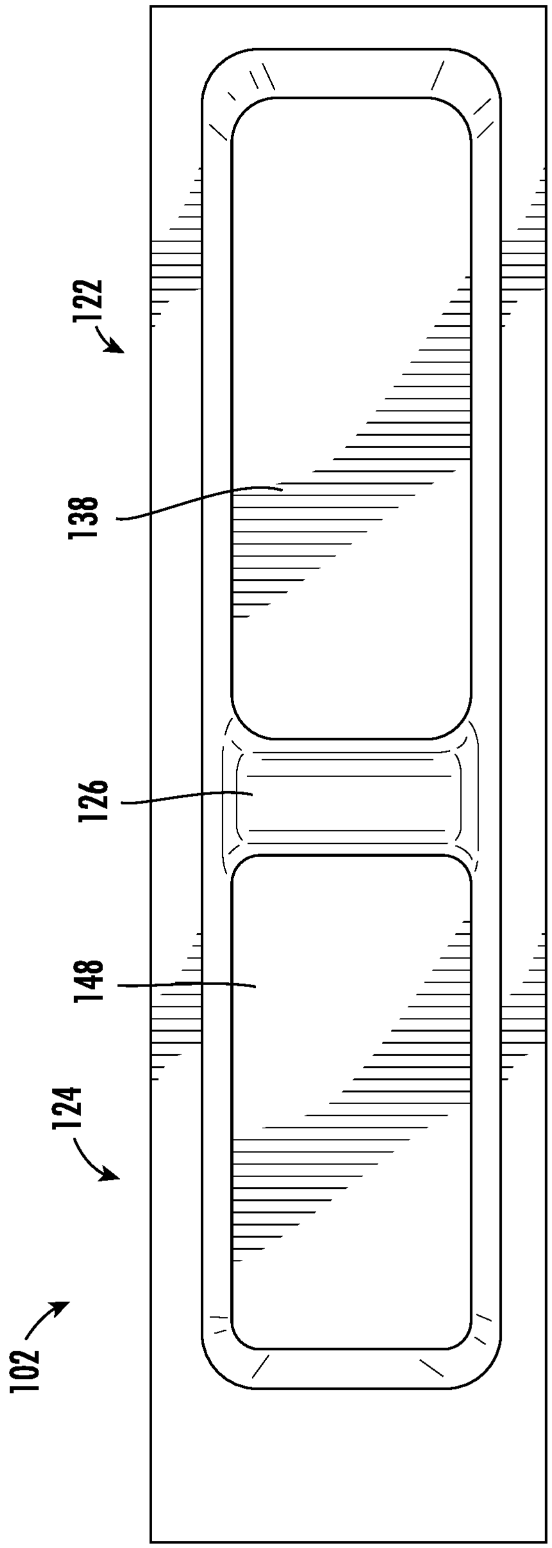
FIG. 9 is a bottom view of the oral care tray of FIG. 3, according to an exemplary embodiment.

As shown in FIGS. 3-9, the first compartment 122 includes a first sidewall 130 and a second sidewall 132 that are separated by a first longitudinal distance L1 (shown in FIGS. 4-5). The first compartment 122 may also include a third sidewall 134 and a fourth sidewall 136 that are separated by a first lateral distance W1 (shown in FIG. 7). In this regard, the first compartment 122 may be defined (e.g., on four sides) by the first sidewall 130, the second sidewall 132, the third sidewall 134, and the fourth sidewall 136, such that the sidewalls 130-136 define an internal space or recess configured to house oral care devices and/or solutions within the first compartment 122. According to an exemplary embodiment, the first longitudinal distance L1 is 4 inches, and the first lateral distance W1 is 2.5 inches. In other embodiments, the first longitudinal distance L1 is another suitable distance (e.g., 1, 1.5, 2, 2.5, 3, 3.5, 4.5, 5, 5.5, etc. inches), and/or the first lateral distance W1 is another suitable distance (e.g., 1, 1.5, 2, 3, 3.5, 4, etc. inches).

The first compartment 122 is also shown to include a first bottom surface 138, according to an exemplary embodiment. The first bottom surface 138 may be spaced apart from the top surface 120 a first vertical distance V1 (shown in FIG. 7), and may be coupled to the sidewalls 130-136 at the edges of the first bottom surface 138. In an exemplary embodiment, the first vertical distance V1 is 2 inches; however, in other embodiments, the first vertical distance V1 is another suitable distance (e.g., 1, 1.5, 2.5, 3, etc. inches). In some embodiments, the sidewalls 130-136 are perpendicular to the first bottom surface 138, so as to form a substantially rectangular space in the first compartment 122. In some embodiments, one or more of the sidewalls 130-136 are angled (e.g., less than 90 degrees, more than 90 degrees, etc.) relative to the first bottom surface 138, so as to form an angled and/or sloped space within the first compartment 122.

As shown in FIGS. 3-9, the second compartment 124 includes a first sidewall 140 and a second sidewall 142 that are separated by a second longitudinal distance L2 (shown in FIGS. 4-5). The second compartment 124 may also include a third sidewall 144 and a fourth sidewall 146 that are separated by a second lateral distance W2 (shown in FIG. 6). Similar to the first compartment 122 discussed above, the second compartment 124 may be defined (e.g., on four sides) by the first sidewall 140, the second sidewall 142, the third sidewall 144, and the fourth sidewall 146, such that the sidewalls 140-146 define an internal space configured to house oral care devices and/or solutions within the second compartment 124. According to an exemplary embodiment, the second longitudinal distance L2 is 3 inches, and the second lateral distance W2 is 2.5 inches. In other embodiments, the second longitudinal distance L2 is another suitable distance (e.g., 1, 1.5, 2, 2.5, 3.5, 4, 4.5, 5, etc. inches), and/or the second lateral distance W2 is another suitable distance (e.g., 1, 1.5, 2, 3, 3.5, 4, etc. inches). In an exemplary embodiment, the first longitudinal distance L1 is greater than the second longitudinal distance L2. In some embodiments, the first longitudinal distance L1 is defined relative to the second longitudinal distance L2 based on characteristics of the oral care system 100 (e.g., a total longitudinal length of the oral care tray 102, a weight of portions of the oral care device 104, a length of the oral care device 104, etc.). In other embodiments, the first longitudinal distance L1 and the second longitudinal distance L2 are the same.

The second compartment 124 is also shown to include a second bottom surface 148, according to an exemplary embodiment. The second bottom surface 148 may be spaced apart from the top surface 120 a second vertical distance V2 (shown in FIG. 6), and may be coupled to the sidewalls 140-146 at the edges of the second bottom surface 148. In an exemplary embodiment, the second vertical distance V2 is 1.5 inches; however, in other embodiments, the second vertical distance V2 is another suitable distance (e.g., 1, 2, 2.5, 3, etc. inches). In some embodiments, the sidewalls 140-146 are perpendicular to the second bottom surface 148, so as to form a substantially rectangular space in the second compartment 124. In other embodiments, one or more of the sidewalls 140-146 are angled (e.g., less than 90 degrees, more than 90 degrees, etc.) relative to the second bottom surface 148, so as to form an angled and/or sloped space within the second compartment 124.

As shown in FIGS. 3-6, in an exemplary embodiment the first bottom surface 138 and the second bottom surface 148 are non-planar. In this regard, the first vertical distance V1 may be greater than the second vertical distance V2. In some embodiments, the first vertical distance V1 and/or the second vertical distance V2 are defined based on characteristics of the oral care system 100 (e.g., a longitudinal length of the oral care tray 102, a weight of portions of the oral care device 104, a length of the oral care device 104, etc.). In some embodiments, the first bottom surface 138 and the second bottom surface 148 are planar. In this regard, the first vertical distance V1 and the second vertical distance V2 may be the same. In yet other embodiments, the first vertical distance V1 and/or the second vertical distance V2 are another suitable relative distance (e.g., the first vertical distance V1 is less than the second vertical distance V2, etc.).

As shown in FIGS. 3-9, the divider 126 separates the first compartment 122 and the second compartment 124, and may be configured to divide the internal spaces of the first compartment 122 and the second compartment 124. As shown in FIGS. 3-5, in an exemplary embodiment the divider 126 forms a first sidewall of the first compartment 122 (e.g., the first sidewall 130) and a second sidewall of the second compartment 124 (e.g., the second sidewall 142). The divider 126 includes a thickness, and where the thickness is a sufficient dimension, the divider also forms a top surface. The divider 126 may extend from the first bottom surface 138 of the first compartment 122 toward the top surface 120, and/or from the second bottom surface 148 of the second compartment 124 toward the top surface 120. In some embodiments, the divider 126 extends from the first bottom surface 138 a first distance, and/or from the second bottom surface 148 a second distance. In an exemplary embodiment, the first distance and the second distance are different due the bottom surfaces 138, 148 being non-planar. In yet other embodiments, the divider 126 does not extend from the second bottom surface 148 of the second compartment 124, such that the divider 126 forms a ledge between the first compartment 122 and the second compartment 124.

In some embodiments, the divider (e.g., the first sidewall 130 and/or the second sidewall 142) is substantially perpendicular to the first bottom surface 138 and/or the second bottom surface 148. In other embodiments, a portion of the divider 126 is angled (e.g., less than 90 degrees, more than 90 degrees, etc.) relative to the first bottom surface 138 and/or the second bottom surface 148, such that the divider 126 forms a slope between the first compartment 122 and the second compartment 124. As discussed briefly above, the divider 126 may also include a thickness and/or a top surface. In some embodiments, the top surface of the divider 126 is substantially parallel to the first bottom surface 138 and/or the second bottom surface 148. In other embodiments, the top surface of the divider 126 is angled relative to the first bottom surface 138 and/or the second bottom surface 148, such that the divider 126 forms a sloped surface between the first compartment 122 and the second compartment 124. In yet other embodiments, the top surface of the divider 126 is rounded or curved.

Figure 10:
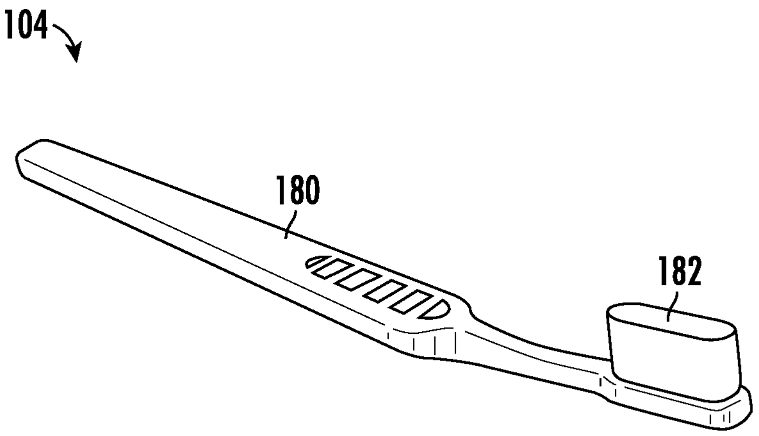
FIG. 10 is a perspective view of an oral care device of the oral care system of FIG. 1, according to an exemplary embodiment.

Referring now to FIG. 10, a perspective view of the oral care device 104 is shown, according to an exemplary embodiment. The oral care device 104 is shown as a toothbrush, and may be configured to receive and/or deliver an oral care product to an oral cavity. The oral care device 104 is shown to include a base 180 and a head 182 coupled to an end of the base 180. The base 180 may be configured to be manipulated (e.g., held, grasped, etc.), such that a user may deliver an oral care product to an oral cavity. The head 182 may be formed of bristles, foam, cloth, a combination thereof, and/or any other suitable material configured to receive and/or provide an oral care product to a user. While the oral care device 104 is shown as a toothbrush, it is understood that any other suitable oral care device may be used (e.g., oral swab, suction swab, bite block, etc.).

Figure 11:
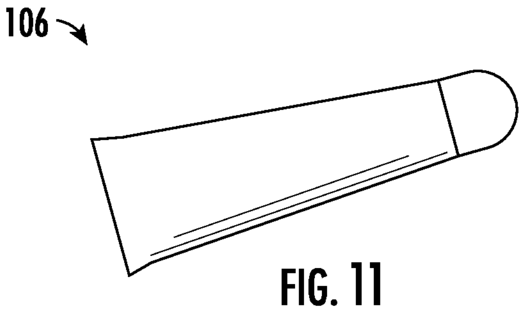
FIG. 11 is a top view of a container of the oral care system of FIG. 1, according to an exemplary embodiment.

Referring now to FIG. 11, a top view of the first container 106 is shown, according to an exemplary embodiment. The first container 106 may be configured to house an oral care product, and selectively release the oral care product in response to being manipulated. According to an exemplary embodiment, the first container 106 is configured to house a mouth moisturizer, and release the mouth moisturizer (e.g., to the oral care device 104) in response to a user manipulating the first container 106. In some embodiments, the first container 106 is configured to house another oral care product, for example hydrogen peroxide solution, antiseptic oral rinse, oral moisturizer spray, mouth paste, etc. Second container 108 may have a similar function and design of first container 106 described above.

Figure 12:
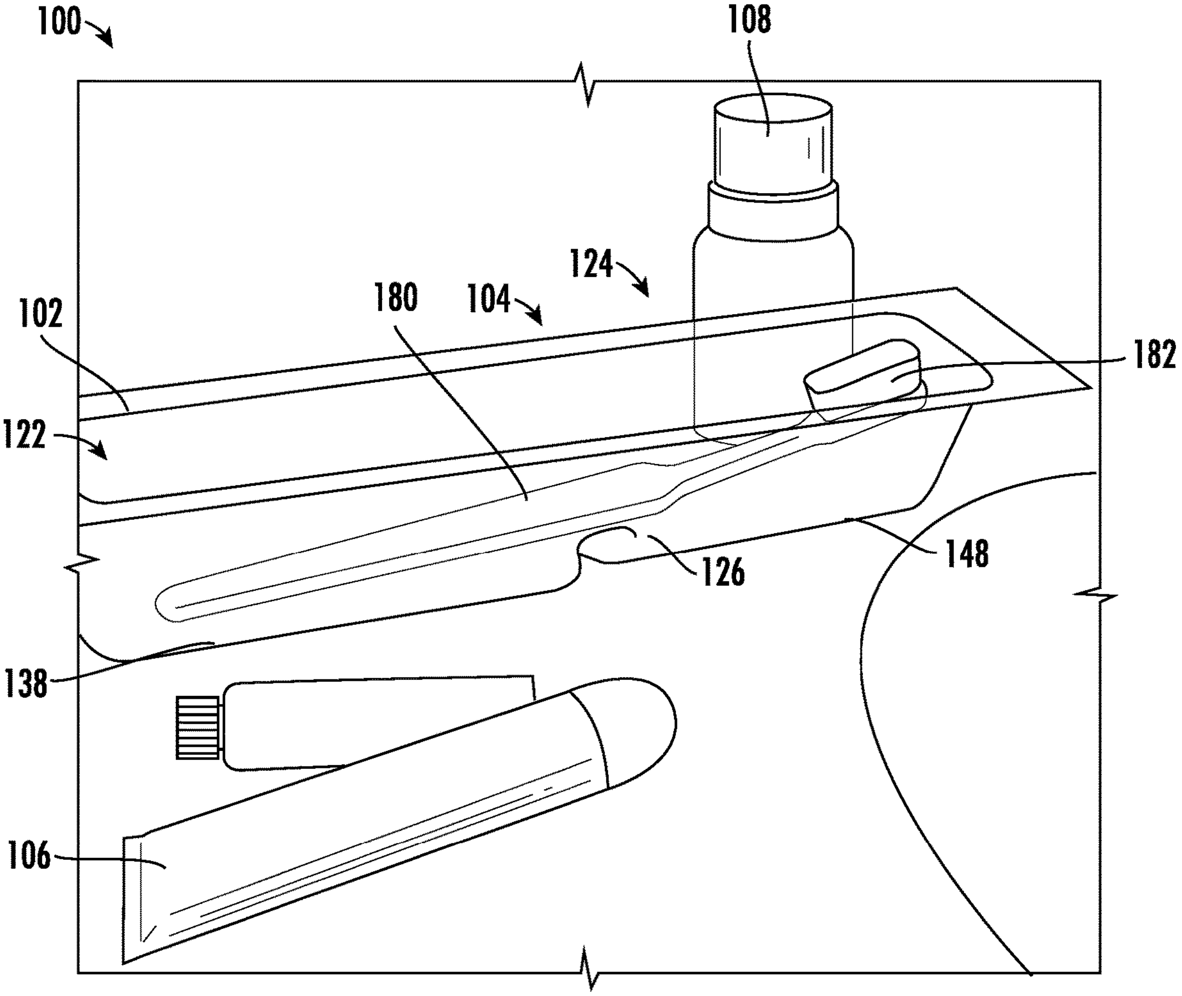
FIG. 12 depicts the oral care system of FIG. 1, where the tray is holding an oral care device between uses, according to an exemplary embodiment.
Figure 13:
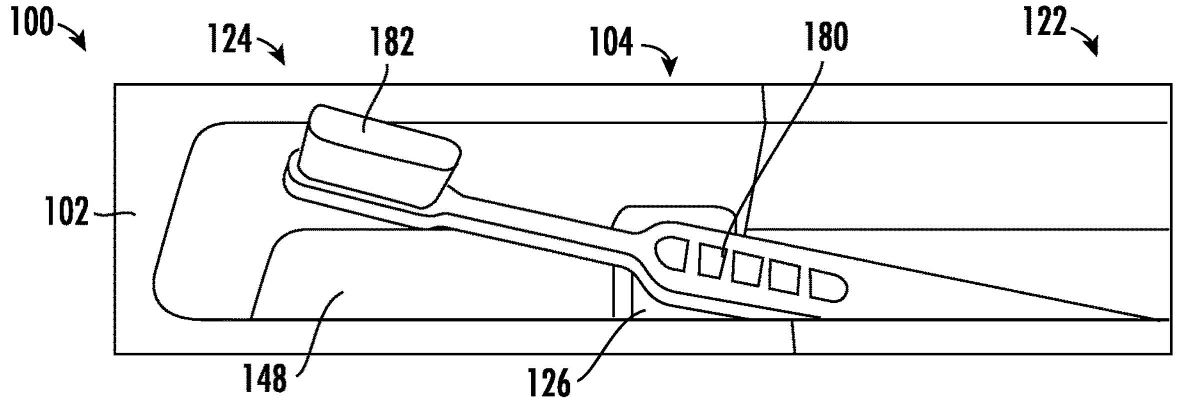
FIG. 13 depicts the oral care system of FIG. 1, where the tray is holding an oral care device between uses, according to an exemplary embodiment.
Figure 14:
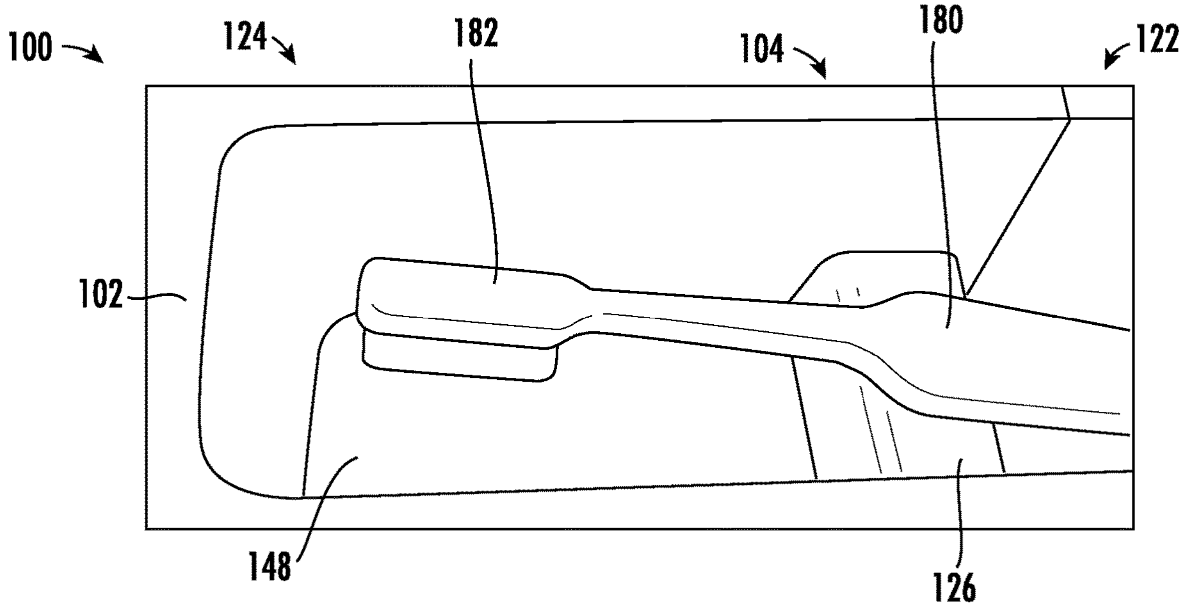
FIG. 14 depicts the oral care system of FIG. 1, where the tray is holding an oral care device between uses, according to an exemplary embodiment.

Referring now to FIGS. 12-14, views of the oral care system 100 in use are shown, according to an exemplary embodiment. As discussed briefly above, prior to use of the oral care system 100, components of the oral care system 100 may be delivered and/or provided as a package or kit. For example, the oral care tray 102 may house the oral care device 104, the first container 106 (e.g., in the first compartment 122, etc.), and/or the second container 108 (e.g., in the second compartment 124, etc.), which may be sealed or packaged for transportation and/or delivery. A user may then use the oral care system 100 to clean and/or provide care within an oral cavity. For example, a user may remove the oral care device 104, the first container 106, and the second container 108 from the oral care tray 102, manipulate the first container 106 and/or the second container 108 to provide an oral care product to the oral care device 104, and use the oral care device 104 to provide the oral care product to an oral cavity.

As shown in FIGS. 12-14, after use of the oral care device 104, the oral care tray 102 may house the oral care device 104, according to an exemplary embodiment. The oral care device 104 may be placed in the first compartment 122, such that a first portion of the base 180 of the oral care device 104 is within the first compartment 122, and a second portion of the base 180 engages the divider 126. In an exemplary embodiment, the oral care device 104 is positioned such that the oral care device 104 is angled relative to the first bottom surface 138, the second bottom surface 148, and/or the divider 126. As shown in FIG. 12, the components of the oral care tray 102 are configured to position the oral care device 104 such that the head 182 is elevated relative to the base 180, and/or the head 182 is positioned away from (e.g., elevated, etc.) the second bottom surface 148. Further, the components of the oral care tray 102 may be configured to position the oral care device 104 such that the head 182 is positioned away from the second bottom surface 148 when the oral care device 104 is facing away from the oral care tray 102 (shown in FIG. 13), and/or when the oral care device 104 is facing toward the oral care tray 102 (shown in FIG. 14). Advantageously, this configuration of the oral care tray 102, and the positioning of the oral care device 104, allows the head 182 to adequately dry (e.g., remove moisture) between uses, and reduces the risk of cross-contamination by ensuring the head 182 does not contact a potentially contaminated surface (e.g., the second bottom surface 148).

In some embodiments, the oral care device 104 is placed in the second compartment 124, such that a first portion of the oral care device 104 is within the second compartment 124 and a second portion of the oral care device 104 engages the divider 126. In this regard, the oral care device 104 may be positioned such that the head 182 is elevated relative to the first bottom surface 138. In other embodiments, the oral care device 104 is positioned such that the head 182 is substantially parallel with the first bottom surface 138 and/or the second bottom surface 148, and/or is positioned away from (e.g., elevated, etc.) the first bottom surface 138 and/or the second bottom surface 148. While housing the oral care device 104 in the oral care tray 102 has been described herein as positioning the oral care device 104 within the first compartment 122 and engaging the divider 126, it is understood that any other suitable arrangement and/or configuration may be used, and any components of the oral care system 100 may include additional, fewer, and/or different working components.

Figure 15:
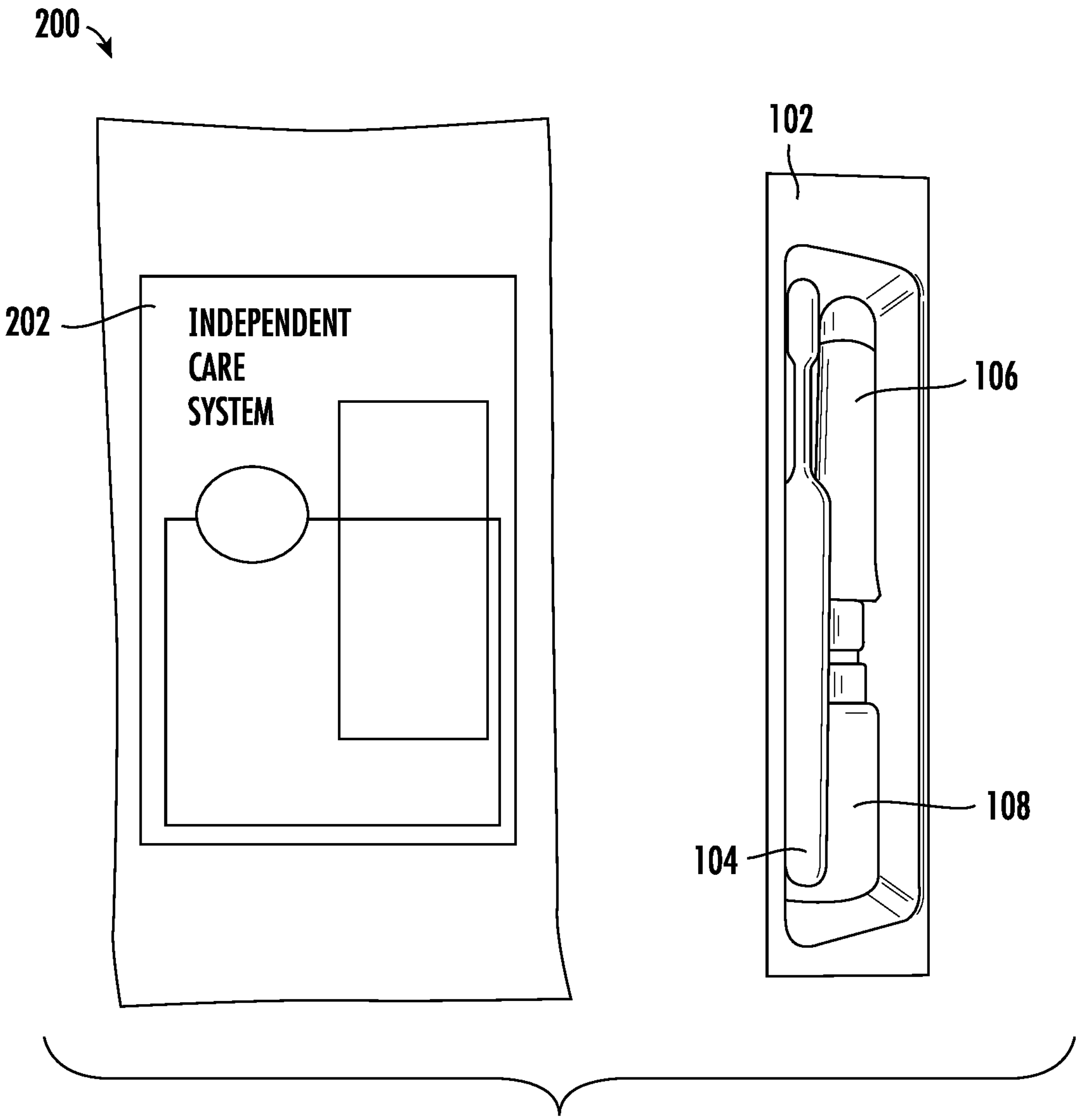
FIG. 15 is a top view of an oral care kit including the oral care system of FIG. 1, according to an exemplary embodiment.

Referring now to FIG. 15, a top view of an oral care kit 200 is shown, according to an exemplary embodiment. In an exemplary embodiment, the oral care kit 200 includes the oral care system 100 of FIGS. 1-11, and a packaging 202. The packaging 202 may house a single oral care system 100, and may be configured to be selectively sealed to protect the oral care system 100 from an outside environment and/or provide access to the oral care system 100. The packaging 202 may be formed of a plastic material (e.g., a high-density polyethylene, linear low-density polyethylene, low density polyethylene, ethylene vinyl alcohol, polylactic acid, thermoplastic elastomer, etc.), and may be any suitable shape and/or size to house the oral care system 100. In some embodiments, the packaging 202 includes other components (e.g., a clip, magnet, hook, etc.) that are configured to aid in positioning, transporting, opening, etc. the oral care kit 200. In some embodiments, the packaging 202 includes more than one oral care system 100.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the systems, apparatuses, and methods shown in the various exemplary embodiments is illustrative only. Additionally, any element disclosed in one embodiment may be incorporated or utilized with any other embodiment disclosed herein. For example, any of the exemplary embodiments described in this application can be incorporated with any of the other exemplary embodiment described in the application. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. An oral care tray comprising:

a first top surface;

a first compartment having a first width, and a first bottom surface on a first plane spaced from the first top surface at a first vertical distance;

a second compartment having a second width, and a second bottom surface on a second plane spaced from the first top surface at a second vertical distance, where the first width and the second width are equal, and the first plane and the second plane are offset; and a divider separating the first compartment and the second compartment thereby forming a first sidewall in the first compartment and a second sidewall in the second compartment, wherein the divider includes a second top surface having a flat profile and extends from the first bottom surface and the second bottom surface toward the first top surface.

2. The oral care tray of claim 1, wherein the first compartment extends a first longitudinal distance and the second compartment extends a second longitudinal distance.

3. The oral care tray of claim 2, wherein the first longitudinal distance is greater than the second longitudinal distance.

4. The oral care tray of claim 1, wherein at least one of the first sidewall or the second sidewall is substantially perpendicular relative to the first bottom surface or the second bottom surface.

5. The oral care tray of claim 1, wherein at least one of the first sidewall or the second sidewall is angled at an angle greater than 90 degrees relative to the first bottom surface or the second bottom surface.

6. The oral care tray of claim 1, wherein the first sidewall and the second sidewall are spaced apart such that the divider includes a thickness defining the second top surface.

7. The oral care tray of claim 6, wherein the second top surface further includes a first connection edge defined by the first sidewall and the second top surface, and a second connection edge defined by the second sidewall and the second top surface.

8. An oral care system comprising:

an oral care device; and an oral care tray configured to house the oral care device, the oral care tray comprising:

a first top surface, a first compartment having a first width, and a first bottom surface spaced from the first top surface at a first vertical distance, the first bottom surface lying on a first plane, a second compartment having a second width, and a second bottom surface spaced from the first top surface at a second vertical distance, the second bottom surface lying on a second plane, where the first width and the second width are equal, and where the first plane and the second plane are offset, and a divider separating the first compartment and the second compartment thereby forming a first sidewall in the first compartment and a second sidewall in the second compartment, wherein the divider extends from the first bottom surface and the second bottom surface toward the first top surface.

9. The oral care system of claim 8, wherein the first compartment is configured to receive a first portion of the oral care device and the divider is configured to engage a second portion the oral care device, such that when the oral care device is received by the first compartment a head of the oral care device is held above the second bottom surface of the second compartment.

10. The oral care system of claim 8, wherein the oral care device is a toothbrush.

11. The oral care system of claim 8, wherein the first compartment extends a first longitudinal distance, and the second compartment extends a second longitudinal distance.

12. The oral care system of claim 11, wherein the first longitudinal distance is greater than the second longitudinal distance.

13. An oral care system comprising:

an oral care device;

a first container configured to house an oral care solution; and an oral care tray configured to house the oral care device, the oral care tray comprising:

a first top surface, a first compartment having a first width, and a first bottom surface spaced from the first top surface at a first vertical distance, the first bottom surface lying on a first plane, a second compartment having a second width, and a second bottom surface spaced from the first top surface at a second vertical distance, the second bottom surface lying on a second plane, where the first width and the second width are equal, and where the first plane and the second plane are offset, and a divider separating the first compartment and the second compartment thereby forming a first sidewall in the first compartment and a second sidewall in the second compartment, wherein the divider extends from the first bottom surface and the second bottom surface toward the first top surface;

wherein the first compartment is configured to receive a first portion of the oral care device, and the divider is configured to engage with a second portion the oral care device, such that when the first portion is received by the first compartment, a head of the oral care device is held above the second bottom surface of the second compartment.

14. The oral care system of claim 13, wherein the oral care solution is one of at least an oral rinse, an oral moisturizer, and an antiseptic solution.

15. The oral care system of claim 13, wherein the head comprises a plurality of bristles, such that when the oral care device is received by the first compartment, the plurality of bristles face away from the second bottom surface.

16. The oral care system of claim 13, wherein the head comprises a plurality of bristles, such that when the oral care device is received by the first compartment, the plurality of bristles face towards from the second bottom surface.

17. The oral care system of claim 13, wherein the divider comprises a second top surface having a flat profile.

18. The oral care system of claim 8, wherein the divider comprises a second top surface having a flat profile.

* * * * *